United States Patent [19]

Sevastyanov et al.

[11] Patent Number: 4,520,826

[45] Date of Patent: Jun. 4, 1985

[54] METHOD FOR GROWTH PROMOTION IN ANIMALS

[75] Inventors: Viktor V. Sevastyanov; Yakov A. Furman; Anatoly P. Grebenschikov, all of Ioshkar-Ola; Viktor F. Lysov, Kazan; Boris N. Shalnov, Ioshkar-Ola, all of U.S.S.R.

[73] Assignees: Mezhkhozyai Stvennoe Opytnokonstruktorskoe Bjuro Mariiskogo Respublicanskogo Proizvodstvennogo Obiedinenia "Mariiskmezhkhozkombikorm"; Mariisky Politekhnichesky Institut, both of Ioshkar-Ola, U.S.S.R.

[21] Appl. No.: 414,715

[22] Filed: Sep. 3, 1982

[51] Int. Cl.³ .............................................. A61N 1/06
[52] U.S. Cl. ..................................... 128/422; 128/804
[58] Field of Search ............ 119/1; 128/419 F, 419 R, 128/422, 804

[56] References Cited

U.S. PATENT DOCUMENTS

| | | | |
|---|---|---|---|
| 2,259,318 | 10/1941 | Mouromtseff | 128/422 |
| 3,181,535 | 5/1965 | Milinowski | 128/422 |
| 4,016,886 | 4/1977 | Doss et al. | 128/422 |

OTHER PUBLICATIONS

Lehmann et al., "Evaluation of a Therapeutic Direct-Contact 915-MHz Microwave Applicator for Effective Deep-Tissue Heating in Humans", IEEE Trans. Microwave Theory and Techniques, vol. MTT-26, No. 8, Aug. 1978, pp. 556-563.

*Primary Examiner*—William E. Kamm
*Assistant Examiner*—Mitchell J. Shein
*Attorney, Agent, or Firm*—Ladas & Parry

[57] ABSTRACT

A method for growth promotion in animals consists in percutaneous application of an electromagnetic field having a frequency of from 25 to 150 MHz and a power of from 30 to 40 W, to the region of the epididymal lobules of the spermatic cords and the epididymides, said application of an electromagnetic field being carried until a subcutaneous induration appears in the aforesaid region, that is, within an exposure time of from 10 to 20 s.

1 Claim, No Drawings

METHOD FOR GROWTH PROMOTION IN ANIMALS

The present invention relates generally to animal husbandry and veterinary medicine and more specifically it concerns a method for growth promotion in animals. The method finds application for growth promotion in males of farm animals aged under 5 months, when under feeding.

Known in the present state of the art are a number of methods for promotion of growth and producing capacity of farm animals. To this end use is made of tissue preparations (biostimulants), antibiotics, food additives, phonotherapy, some medicinal substances.

There is also known a method for growth promotion in young animals (cf. Problems of experimental physiology, Proceedings of the Uzbek State Research Institute for Physiotherapy and Health Resort Therapy named after N. A. Semashko, issue X, the N. A. Semashko Institute PH, Tashkent 1948, pp. 113 through 119). Experiments were conducted on rabbits. The essence of the method resided in that 10 to 12-days old rabbits were exposed to the effect of a VHF electric field, that is, were placed in a "capacitor field" established between two metallic plates, wavelengths were varied within 1.5 to 7.5 m, the number of sessions, 25, the exposure time, 3 min, dimensions of an electrode, 24×13 cm, the distance between a rabbit and any of the plates, 1.5 to 2 cm. A gain in weight was observed after the 5th session and became very appreciable to the end of the experiment. The weight increment of the experimental rabbits exceeded that of the control group of animals by 25 to 30 percent within the experiment period.

The aforesaid method, however, failed to find industrial application due to its being too labourious for technological implementation. Furthermore said method involves electromagnetic effect upon the animal's organism as a whole, which would subsequently affect adversely the functional state of the systems of the animal's organism.

It is therefore a primary object of the present invention to provide a method for growth promotion in animals, which makes it possible to attain higher gain in weight of animals using simplified technology with reduced food consumption per weight increment unit.

The aforesaid object is accomplished due to the fact that a method for growth promotion in animals, according to the invention, consists in percutaneous application of an electromagnetic field having a frequency of from 25 to 150 MHz and a power of from 30 to 40 W, to the region of the epididymal lobules of the spermatic cords and the epididymides, said application of an electromagnetic field being carried out till a subcutaneous induration appears in the aforesaid region, that is, within an exposure time of from 10 to 20 s.

The method proposed in the invention is carried out as follows.

The epididymal lobules of the spermatic cords and the epididymides are exposed to the effect of an electromagnetic field of the radiofrequency range (25 to 150 MHz), applied with the use of various construction electrodes, e.g., of the capacitor type, or a solenoid. An r.f. generator having a power of from 30 to 40 W is used, the exposure time being within 10 to 20 s. The effect may be considered to be positive when a subcutaneous induration appears after the exposure in the zone having been exposed, with the resultant temporary disorder of the innervation of the blood and lymph circulation. As a result some inconsiderable edema of the tests and the scrotal tissue becomes visually perceptible on the second day after the exposure, which disappears in 7 to 14 days, and the function of the testes is restored. The method is more readily applicable to the males of farm animals featuring externally located testes. The mode of action of the method proposed is explainable by the feedback mechanism of the hypothalamic-hypophyseal region of the brain with the gonads. Neurosecretory cells of the hypothalamic-hypophyseal region are susceptible to the afferent signals received from some other divisions of the nervous system, and are capable of sending their efferent humoral impulses as neurohormones, thus transforming the initial nervous impulse into a hormonal link, which influences the metabolism, somatic growth, etc. As a result such influence enables more prolonged effect to be obtained. Histologic examinations of the testicles of bull-calves of the control and experimental groups carried out 1 to 1.5 months after the animals had been exposed to the effect of an r.f. electromagnetic field, gave evidence that no substantial changes could be observed to have resulted from the stimulation applied to the test animals compared to the control ones at a given term of slaughter, as judged by micromorphology of the testicles with allowance for architectonics of the seminiferous tubules, the length of the spermatozoa, their heads, cytologic composition of the spermatogenic epithelium and degree of differentiation of the spermatozoa before their formation as observed under an optical microscope.

The testes of both test and control bulls were found to exhibit completed spermatogenesis, featuring moderate physiological decomposition of the spermatogenic cells and spermatozoa. No pathologic changes whatever were detected in the testes of the test bulls exposed to the effect of an electromagnetic field, nor any morphologic criteria indicative of hyperfunction of the organ.

The proposed method was tested experimentally on bull-calves aged from 3 to 5 months and on ram-lambs of 2.5 to 3 months old. The method is instrumental in higher weight increment of animals beginning with the second or third month after the exposure. A considerable effect is attained on the third month after the exposure, the weight increment being increased up to 12 percent on the average. Two months after the exposure an appreciable difference in feeding capacity becomes evident, that is, the animals of the test group eat and digest fodder better than those of the control group, and less food consumption per weight increment unit is observed for the test group.

For a better understanding of the invention reference is had to some specific variants of tests carried out.

EXAMPLE 1

Bull-calves aged 3 to 5 months subdivided into the test and control groups (16 animals in each) were exposed to the effect of r.f. range (25 to 150 MHz) electromagnetic field having a power of from 30 to 40 W. The exposure time was 10 to 20 s until a subcutaneous induration appeared in the exposed zone. The animals were weighed in a month after the exposure. 1 to 1.5 months after the exposure there were carried out histologic examinations of the testicles of the test and control animals. The test results are tabulated below. A mathematical analysis has demonstrated that a difference in average weight increment between the control and test groups is of systematic nature and confirms the presence of a stimulation effect.

EXAMPLE 2

Exposed to the effect of an r.f. range electromagnetic field were ram-lambs aged from 2.5 to 3 months. A test and a control group numbered 20 animals each.

The animals were fed in groups and weighed individually. In a month after the exposure three animals from the test group and the same number of the control animals were subjected to metabolic investigation, whereupon biochemical blood analysis was carried out. The animals were fed with mixed feed and grass pellets. An analysis into weight increments for an experimental period (95 days) demonstrated that within the third month after the exposure to the effect of an electromagnetic field the animals of the test group featured the intensity of the weight increment rise 30 percent higher than that in the control animals. The minimum mixed-feed consumption per kg of the weight increment was 21 percent less in the test animals as compared to those of the control group. The animals of the test group digested and assimilated mixed feed better than the control animals. A difference in utilization of mixed feed per kg of the weight increment marked especially clearly in two months after the exposure to the effect of an electromagnetic field, that is, 4.76 kg per kg of the weight increment in the control group and 3.24 kg in the test group. In terms of fodder units the animals of the test group consumed a lower amount of fodder units per kg of the weight increment than the control animals did. Especially markedly pronounced was the difference in such an index within the third month of the experiment, when the control animals consumed 7.44 fodder units per kg of the weight increment, whereas the test animals, only 5.56, i.e., by 1.88 fodder units less.

TABLE

COMPARISON TABLE OF THE RESULTS OF THE GROWTH PROMOTION TEST IN BULL-CALVES AGED FROM 3 TO 5 MONTHS

| Group 1 | Average weight at the beginning of test 2 | Average weight at the end of test 3 | Average weight increment values June 4 | July 5 | Average weight increment values August 6 | September 7 | Average monthly weight increment 8 | Average percentage increase in weight increment 9 | RMS deviation of weight increment 10 |
|---|---|---|---|---|---|---|---|---|---|
| Test | 113.25 | 241.9 | 19.625 | 31.5 | 34.5 | 43 | 32.156 | 9.3 | 9.82 |
| Control | 121.25 | 238.86 | 11.56 | 30 | 33.87 | 42.18 | 29.40 | | 12.92 |
| Difference | 8 | 3.04 | 8.065 | 1.5 | 0.63 | 0.82 | 2.76 | | |

What we claim is:

1. A method for growth promotion in animals, consisting in percutaneous application of an electromagnetic field having a frequency of from 25 to 150 MHz and a power of from 30 to 40 W, to the region of the epididymal lobules of the spermatic cords and the epididymides, said application of an electromagnetic field being carried out until a subcutaneous induration appears in the aforesaid region, that is, within an exposure time of from 10 to 20 s.

* * * * *